US006426342B2

(12) United States Patent
Koppel

(10) Patent No.: US 6,426,342 B2
(45) Date of Patent: Jul. 30, 2002

(54) USE OF β-LACTAMASE INHIBITORS AS NEUROPROTECTANTS

(75) Inventor: Gary A. Koppel, Indianapolis, IN (US)

(73) Assignee: Revaax Pharmaceuticals, LLC, Indianapolis, IN (US)

(*) Notice: Subject to any disclaimer, the term of this patent is extended or adjusted under 35 U.S.C. 154(b) by 0 days.

(21) Appl. No.: 09/782,507

(22) Filed: Feb. 13, 2001

Related U.S. Application Data

(63) Continuation-in-part of application No. 09/640,363, filed on Aug. 16, 2000.
(60) Provisional application No. 60/149,115, filed on Aug. 16, 1999, provisional application No. 60/172,452, filed on Dec. 17, 1999, provisional application No. 60/176,570, filed on Jan. 18, 2001, and provisional application No. 60/194,534, filed on Apr. 14, 2000.

(51) Int. Cl.$^7$ .................. A61K 31/395; A61K 31/43
(52) U.S. Cl. ................. 514/210.06; 514/192; 514/193; 514/210.1
(58) Field of Search .................... 514/210.06, 192, 514/193, 210.1

(56) References Cited

U.S. PATENT DOCUMENTS

| 4,268,503 A | 5/1981 | Imanaka et al. |
| 4,302,447 A | 11/1981 | Horrobin |
| 4,594,247 A | 6/1986 | Brier |
| 5,763,603 A | 6/1998 | Trickes |
| 5,795,877 A | 8/1998 | Jackson et al. |
| 5,824,662 A | 10/1998 | Slusher et al. |
| 5,863,536 A | 1/1999 | Jackson et al. |
| 5,880,112 A | 3/1999 | Jackson et al. |
| 5,905,076 A | 5/1999 | Singh et al. |
| 5,912,242 A | 6/1999 | Pevarello et al. |
| 5,968,915 A | 10/1999 | Jackson et al. |
| 5,977,090 A | 11/1999 | Slusher et al. |
| 6,004,946 A | 12/1999 | Slusher et al. |
| 6,015,809 A | 1/2000 | Zhu et al. |
| 6,017,903 A | 1/2000 | Slusher et al. |

FOREIGN PATENT DOCUMENTS

| GB | 1 508 977 | 4/1979 |
| WO | WO 95/20980 | 8/1995 |
| WO | WO 97/10247 | 3/1997 |

OTHER PUBLICATIONS

"The Relation Between Fear Induced by Novel Stimulation and Exploratory Behavior" by K.C. Montogomery J. Comp. Physiol. Psychol. (1955) vol. 48, 254–260.

"Action of Penicillin on Inhibitory Processes in the Cat's Cortex" by H.V. Duijn, P.A. Schwartzkroin, and D.A. Prince, Brain Res. (1973) vol. 53, 470–476.

"Convulsant Actions of Penicillin: Effects on Inhibitory Mechanisms" by H. Meyer and D. Prince (1973) vol. 53, 477–482.

"Penicillin Decreases Chloride Conductance in Crustacean Muscle: A Model for the Epileptic Neuron" by B. Hochner, M.E., Spira, and R. Werman. Brain Res. (1976) vol. 107, 85–103.

A.B. Chernomordik. Klin. Med. (1980) vol. 2. 102–105.

"Antagonism by Penicillin of Gamma–Aminobutyric Acid Depolarizations at Presynaptic Sites in Rat Olfactory Cortex and Cuneate Nucleus In Vitro" by H.G. Pickles and M.A. Simmonds, Neuropharmacology (1980) vol. 19, 35–38.

"GABA and the Behavioral Effects of Anxiolytic Drugs" D.J. Sanger, Life Sciences (1985) vol. 36, 1503–1513.

"Convulsant Doses of Penicillin Shorten the Lifetime of GABA–Induced Channels in Cultured Central Neurones" by P. Chow and D. Mathers, Br. J. Pharmac. (1986) vol. 88. 541–547.

"N–methyl–D–aspartate Receptors and the Enhancement of Somatosensory Evoked Potentials in Penicillin Epileptogenesis in Rats" by Z.J. Bashir and O. Holmes, Physiological Society (1987) 19P.

"Competitive Inhibition of N–Acetylated–alpha–Linked Acidic Dipeptidase Activity by N–Acetyl–L–Aspartyl–beta–Linked L–Glutamate" by V. Serval. L. Barbeito, A. Piltaluga, A. Cheramy, S. Lavielle, and J. Glowinski, J. Neurochemistry (1990) vol. 55, 39–46.

"Time Course of Interictal EEG Patterns Induced by a Penicillin Injection into the Olfactory Cortex" by E. Horn, K. Esseling, and R. Wagner, Pharmacology Biochemistry & Behavior (1991) vol. 40, 351–357.

"The Pharmacology of Recombinant GABA, Receptors Containing Bovine alphal. betal, gamma2L Sub–units Stably Transfected into Mouse Fibroblast L–cells" by A.L. Home, K.L. Hadingham, A.J. Macaulay, P. Whiting and J.A. Kemp, Br. J, Pharmacology (1992) vol. 107, 732–737.

I.V. Batueva N.P. Vesclkin, and R. Veskov, Neirofiziologiya (1992) vol. 24, (2), 151–160.

"Increased Intra–and Extracellular Concentrations of Gamma–Glutamylglutamate and Related Dipeprides in the Ischemic Rat Striatum: Involvement of Gamma–Glutamyl Transpeptidase" by O. Orwar, X. Li, P. Andine, C.M. Bergström, H. Hagberg, S. Folestad, and M. Sandberg, J. Neurochemistry (1994) vol. 63, 1371–1376.

"Endogenous Gamma–L–Glutamyl and Beta–L–Aspartyl) Peptides and Excitatory Aminoacidergic Neurotransmission in the Brain" by V. Varga, R. Janaky, P. Saransaari, and S.S. Oja. Neuropeptides (1994) vol. 27, 19–26.

(List continued on next page.)

Primary Examiner—William R. A. Jarvis
(74) Attorney, Agent, or Firm—Barnes & Thornburg

(57) ABSTRACT

Novel neuroprotectant methods are described. β-Lactamase inhibitors are used to prevent or reduce loss of neuronal cells and neuronal cell function in patients afflicted with or susceptible to disease states or conditions known to result in or cause neuronal tissue insult.

4 Claims, No Drawings

OTHER PUBLICATIONS

"Penicllins and Their Derivatives: Antiulcer/Antistress Properties?" by A. V. Kalueff, G.E. Samonina, and I.P. Ashmarin, Neuropschychopharmacology (1994) vol. 10, 272S.

"Behavioral Effects of Penicillin in a Test for Anxiety in Rats" by A. V. Kaluev, G.E. Samonina and I.P. Ashmarin. Bulletin of Experimental Biology and Medicine (1995) vol. 120, 984–986.

"Design, Synthesis , and Biological Activity of a Potent Inhibitor of the Neuropeptides N–Acetylated Alpha–Linked Acidic Dipeptidase" by P.F. Jackson, D.C. Cole, B.S. Slushes, S. Stetz, L.E. Ross, B.A. Donzanti, and D.A. Trainor, J. Med. Chem. (1996) vol. 39(2), 619–622.

"Gamma–L–Glutamyl–L–Aspartate Induces Specific Deficits in Long–Term Memory and Inhibits [$^3$H] Glutamate Binding on Hippocampel Membranes" by A. Ungerer, M.S. Bourgeois, C. Mélan, Y. Boulanger, J. Reinbolt, I. Amiri, and J.D. Barry, Brain Res. (1988) vol. 446, 205–211.

nE.F. Reynolds, "Martindale, The Extra Pharmocopoeia, "*Royal Pharmaceutical Society*, London, p. 211, Column 2–3, (1996) XP–00216510.

Passani, Lucius A., "N–acetylaspartylglutamate, N–acetylaspartate, and N–acetylated alpha–linked acidic dipeptidase in human brain and their alterations in Huntington and Alzheimer diseases," *Molecular and Chemical Neuropathology*, vol. 31, No. 2, pp. 97–118, (1997) XP–000987254.

Macknin, M.L., "Behavioral changes after amoxicillin–clavulanate," letter, *Pediatric Infectious Disease Journal*, vol. 6, No. 9, (Sep. 1987) XP–000987254.

Tsai, Guochuan, et al., "Abnormal Excitatory Neurotransmitter Metabolism in Schizophrenic Brains", *Archives of General Psychiatry*, vol. 52, No. 10, pp. 829–636, (1995) XP–00987256.

Pangalos, Menelas N., et al, "Isolation and expression of novel human glutamate carboxypeptidases with N–acetylated alpha–linked acidic dipeptidase and dipeptidyl pepetidase IV activity" *Journal of Biological Chemistry*, vol. 274, No. 13, pp. 8470–8483 (Mar. 26, 1999), XP–002161509.

USE OF β-LACTAMASE INHIBITORS AS NEUROPROTECTANTS

CROSS-REFERENCE TO RELATED APPLICATIONS

This application is a continuation-in-part of U.S. Ser. No. 09/640,363, filed Aug. 16, 2000, which claims priority to U.S. Provisional Applications Nos. 60/149,115, filed Aug. 16, 1999; 60/172,452, filed Dec. 17, 1999; 60/176,570, filed Jan. 18, 2001, and 60/194,534, filed Apr. 14, 2000.

FIELD OF THE INVENTION

This invention relates to a new use of inhibitors of bacterial β-lactamases. More particularly, this invention is directed to the use of β-lactamase inhibitors for preventing or reducing neuronal damage in patients suffering from or susceptible to disease states characterized by loss of neuronal cells or loss of neuronal cell function.

BACKGROUND OF THE INVENTION

Over excitation of NMDA receptor channel complexes on post-synaptic neurons following excessive release of glutamic acid from synaptozones and glial cells results in massive calcium ion influx into neuronal cells leading to their death. This is believed to occur under conditions such as stroke, hypoglycemia, cardiac arrest, and other hypoxic or ischemic processes, including, for example, neural trauma, and perinatal asphyxia. Other conditions known to result in or from loss of neuronal cells or loss of neuronal function include seizure activity such as that associated with epilepsy, amyliotrophic lateral sclerosis (ALS), Alzheimer's disease, Huntington's disease, Parkinsonism and dementia such as multi-infarct dementia, vascular dementia, and neurodegenerative dementia. Other conditions known to result in loss of neuronal cells or loss of neuronal cell function are those generally characterized as secondary neurodegenerative disease of typically metabolic or toxic origin. While significant progress has been made in developing therapeutics for treatment or prevention of such neurodegenerative conditions or disease states, there still exists significant need for the development of alternative therapies for treatment of patients afflicted with such conditions.

SUMMARY OF THE INVENTION

Accordingly, the present invention provides a surprisingly effective neuroprotective therapy. It is based on the discovery that compound capable of inhibiting the activity of bacterial β-lactamases (i.e., β-lactamase inhibitors) is, as well, a powerful neuroprotective agent. The invention thus provides a method for preventing neuronal damage or the progression of neuronal damage in a patient suffering from or susceptible to said damage, characterized generally as a loss of neuronal cells or a loss of neuronal cell function, such as that secondary to the occurrence of strokes, seizures, neural trauma, and a multiplicity of neuro-degenerative disease states of widely variant etiology.

In another embodiment of the invention there is provided a neuroprotective pharmaceutical composition and a method for manufacturing same using a β-lactamase inhibitor as the active ingredient. Such pharmaceutical compositions can be formulated in unit dosage forms adapted for patient delivery by a wide variety of routes of administration including, but not limited to, oral ingestion, buccal, sublingual, parenteral, transdermal and rectal routes of administration. In one embodiment the dosage forms are formulated for controlled release of the β-lactamase inhibitor.

DETAILED DESCRIPTION OF THE INVENTION

This invention provides a method for the treatment of a patient suffering from or susceptible to a condition known to result in loss of neuronal cells or loss of neuronal cell function. It comprises the step of administering to a patient in need of such treatment a neuroprotective amount of a bacterial β-lactamase inhibitor. The method is effective to reduce loss of neuronal cells or neuronal cell function resulting from the patient condition. The method effectively prevents neuronal damage or the progression of neuronal damage in patients suffering from or susceptible to disease states causing such neuronal damage. It has been reported that blocking the neurogenic enzyme N-acetylated-a-linked acidic dipeptidases (NAALADases) in the brain reduces ischemic brain injury. Blocking NAALADase reduces high levels of glutamate that follow, for example, ischemic stroke, protecting the brain from the neurotoxic effects of high glutamate levels in neuro-tissues. It has been discovered that clavulanic acid, a recognized β-lactamase inhibitor, also is a potent inhibitor of NAALADase. Based on that initial discovery, and a subsequent comparison of the putative active sites of so-called "serine" β-lactamases (Class A, C and D), and conserved amino acid sequence for rat and human NAALADase, it was determined that there is an almost perfect overlap of the putative active sites of serine β-lactamases and key sequences of NAALADase. Since β-lactamase inhibitors are believed to inhibit β-lactamase activity by binding to the β-lactamase to alter or block the putative four active site motif on β-lactamase, one can infer that the similarity in active site sequence and location would confer similar binding properties of other known β-lactamase inhibitors to NAALADase or be a molecular signature of an enzyme derived from β-lactamase, such as NAALADase, which may bind inhibitors by some other modified active site motif.

There are many compounds that are reported in the literature to exhibit the capacity to inhibit bacterial β-lactamase activity. Such is typically measured by the compound's ability to inhibit the rate of hydrolysis of a penicillin or cephalosporin substrate by 50%, either with or without preincubation. Techniques for assessing or assaying β-lactamase inhibition are well known in the art.

Most known β-lactamase inhibitors are compounds which themselves comprise a β-lactamase ring structure. Both the patent and non-patent art are replete with reference to such compounds, their preparation, and their mechanism of action. Inhibition of bacterial β-lactamase can occur either by an irreversible mechanism or via a reversible mechanism involving a transient inhibited intermediate in which the β-lactamase inhibitor binds to and thus blocks the active site on the β-lactamase molecule. β-lactamases can be inhibited irreversibly by a β-lactamase inhibitor which competitively or preferentially binds to the active site on the β-lactamase molecule where it effectively acylates the β-lactamase as a first step in deactivating the enzyme.

Exemplary of known β-lactamase inhibitors in commercial use are clavulanic acid, sulbactam, and tazobactam. Other known β-lactamase inhibitors include derivatives or analogs of clavulanic acid including deoxyclavulanic acid isoclavulanic acid, 9-deoxyclavulanic acid. 9-amino deoxyclavulanic acid, and other clavulanic acid derivatives such as those wherein the 9-hydroxy group has been chemically modified (e.g. as an acetate, n-methyl carbamate, methyl ether, benzyl ether, or thiomethyl ether). Sulbactam has been used to prepare prodrugs, for example, sultamacillin which is absorbed from the gastrointestinal tract and then hydrolyzed into sulbactam and ampicillin. Other known β-lactam containing compounds known to possess β-lactamase inhibitor properties include olivanic acids and thienamycin of the carbapenem family of novel naturally occurring β-lactam antibiotics.

One preferred β-lactamase inhibitor for use in accordance with the present invention is clavulanic acid. It has only weak, though broad spectrum antibacterial activity, and it has a long record of safe use as a β-lactamase inhibitor in commercially available combinations with amoxycillin and ticarcillin. Moreover, it exhibits good oral adsorption and transport across the blood-brain barrier into the cerebral spinal fluid. β-lactamase inhibitors can be administered in accordance with this invention as their pharmaceutically acceptable salts or as bioactive esters which hydrolyze to provide therapeutic concentrations of the β-lactamase inhibitor upon patient administration.

A β-lactamase inhibitors is used in accordance with the present invention in a method of treatment of a patient suffering from or susceptible to a condition known to result in a loss of neuronal cells or loss of neuronal cell function. Thus it can be used to prevent such disease, disorder or condition from occurring in an animal or patient that may be susceptible to the disease, or disposed to develop the disease, but has not yet been diagnosed as having the disease or has not yet developed symptoms of the disease. More typically it is used to treat patients to relieve symptoms or cause regression of the disease or condition after its occurrence. Conditions known to result in loss of neuronal cells or loss of neuronal cell function include conditions such as stroke, hypoglycemia, cardiac arrest, or by other hypoxic or ischemic processes, including, for example, neural trauma or accident and perinatal asphyxia. Other conditions known to result in or from loss of neuronal cells or loss of neuronal function include seizure activity, such as that associated with epilepsy, ALS, Alzheimer's disease, Huntington's disease, Parkinsonism, and various forms of dementia such as multi-infarct dementia, vascular dementia, and neurodegenerative dementia. Loss of neuronal cells or loss of neuronal cell function can also derive from conditions generally characterized as secondary neurodegenerative diseases, typically of metabolic or toxic origin. Patients can be treated in accordance with this invention responsive to observation of such disease states, or patients to prevent loss of neuronal cells or loss of neuronal cell function in patients disposed to or susceptible to develop conditions known to affect neuronal cells.

"Neuronal cells" as used herein refer to those cells that make up the nervous system including, for example, neurons, neural support cells, glia, Schwann cells, cells comprising the vasculature contained within and supplying such cells within the central nervous system including the brain, the brain stem, the spinal cord, and the peripheral nervous system.

"Neuroprotective" as used in describing and defining the present invention refers to the effect of preventing, arresting or ameliorating damage to neuronal cells in patients afflicted with conditions known to affect such cells. The term also refers to the capacity or function to protect and/or revive cells which have suffered damage or which are or have been exposed to cell damaging conditions.

Effective dosages of the β-lactamase inhibitors when used in accordance with the method of this invention depends on patient condition and the method of administration. Animal tests indicate that clavulanic acid is an effective neuroprotectant when administered intraperitoneally at a dose of about 1 μg/kg to about 50 μg/kg. Parenteral doses of β-lactamase inhibitors when used in accordance with this invention range from about 0.02 to about 20 mg/kg. Oral dosage levels are typically higher, ranging from about 0.1 mg/kg to about 50 mg/kg. The dosage levels can be adjusted higher or lower by the attending physician depending oil patient condition and the observed clinical response to the initial dosage. Treatment in accordance with this invention typically includes one to four daily doses of β-lactamase inhibitor. Formulation of the inhibitor into controlled release dosage forms (either for parenteral or oral use) enables effective once or twice a day dosage protocols.

The β-lactamase inhibitor treatment can be administered in the method of the present invention orally, parenterally, by inhalation spray, topically, rectally, nasally, bucally, vaginally or via an implanted reservoir in a dosage formulation containing conventional non-toxic pharmaceutically acceptable carriers, adjuvants and vehicles. Oral administration is preferred, however parenteral administration may be considered more appropriate/effective where the patient condition is acute. Administration of the β-lactamase inhibitor is typically continued until patient condition is normalized or until a patient is determine to be no longer susceptible to or disposed to developing or redeveloping the neurodegenerative condition. Dosage administration can be continued using the same or attenuated dosage protocol for prophylaxis of the patient condition.

In another embodiment of the present invention there is provided a neuroprotective pharmaceutical composition consisting essentially of a neuroprotective amount of a β-lactamase inhibitor and a pharmaceutically acceptable carrier therefor. In one embodiment the pharmaceutical composition is prepared in a unit dosage form, for example, a tablet, capsule or caplet for oral dosage form.

In accordance with one embodiment of this invention there is provided a method of manufacturing a pharmaceutical composition useful for preventing neuronal damage or the progression of neuronal damage in a patient suffering from or susceptible to such damage. The method comprises the step of preparing a pharmaceutical mixture consisting essentially of a β-lactamase inhibitor and a pharmaceutical acceptable carrier. Portions of the mixture are then used to prepare unit dosage forms containing a neuroprotective amount of the β-lactamase inhibitor. The component β-lactamase inhibitor can be in acid or pharmaceutically acceptable salt form or, for example, as a biodegradable ester.

Examples of suitable in vivo hydrolysable (active) ester groups include, for example, acyloxyalkyl groups such as acetoxymethyl, pivaloyloxymethyl, β-acetoxyethyl, β-pivaloyloxyethyl, 1-(cyclohexylcarboonyloxy) prop-1-yl, and (1-aminoethyl) carbonyloxymethyl; alkoxycarbonyloxyalkyl groups, such as ethoxycarbonyloxymethyl and alpha-ethoxycarbonyloxyethyl; dialkylaminoalkyl groups, such as ethoxycarbonyloxymethyl and β-ethoxycarbonyloxyethyl; dialkylaminoalkyl especially di-lower alkylamino alkyl groups such as dimethylaminomethyl, dimethylaminoethyl, diethylaminomethyl or diethylaminoethyl:2-(alkoxycarbonyl)-2-alkenyl groups such as 2-(isobutoxycarbonyl) pent-2-enyl and 2-(ethoxycarbonyl)but-2-enyl; lactone groups such as phthalidyl and dimethoxyphthalidyl; and esters linked to a second β-lactam antibiotic or to a β-lactamase inhibitor.

Suitable pharmaceutically acceptable salts of β-lactamase inhibitors used as neuroprotectants in this invention include metal salts, e.g. aluminum, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylidene, bis-(2-hydroxyethyl)amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other useful salts include the lithium salt and silver salt.

The amount of β-lactamase inhibitor used to form the pharmaceutical composition is that amount effective to provide upon delivery by the intended route of administration, a neuroprotective concentration of the inhibitor in the neuronal tissue where protection is desired. Parenteral dosage forms typically can contain about 0.5 to about 50 mg/dose or 2- to 3-fold that amount when formulated in a controleld release parenteral dosage form, while oral dosage forms can typically contain about 1 to about 200 mg of β-lactamase inhibitor. Neuroprotective amounts of β-lactamase inhibitors in other dosage forms can be determined by routine experimentation based inter alia on absorption efficiency and rate of absorption of the β-lactamase inhibitor by such routes of administration.

β-lactamase inhibitors for use in accordance with this invention can thus be combined with one or more pharmaceutically acceptable carriers and may be administered, for example, orally in such forms as tablets, capsules, caplets, dispersible powders, granules, lozenges, mucosal patches, sachets, and the like. In such formulations a β-lactamase inhibitors is combined with a pharmaceutically acceptable carrier, for example starch, lactose or trehalose, alone or in combination with one or more formulation excipients and pressed into tablets or lozenges or filled into capsules. Optionally, dosage forms intended for oral ingestion administration such as tablets, caplets or capsules can be enterically coated to minimize hydrolysis/degradation in the stomach. In another embodiment the dosage form is formulated for oral administration, and is formed as a prolonged release dosage form using art-recognized formulation techniques for release the β-lactamase inhibitor over a predetermined period of time.

Topical dosage forms, including transdermal patches, intranasally and suppository dosage unit formulations containing the β-lactamase inhibitor and conventional non-toxic pharmaceutically acceptable carriers, adjuvants and vehicles adapted for such routes of administration can also be used in the present neuroprotective method.

The pharmaceutical compositions suitable for injectable use in accordance with ths invention include sterile aqueous solutions or dispersions and sterile powders or lyopholysates for the extemporaneous preparation of sterile injectable solutions or dispersions. The dosage forms must be sterile and it must be stable under the conditions of manufacture and storage. The carrier for injectable formulations is typically water but can also include ethanol, a polyol (for example, glycerol, propylene glycol and liquid polyethylene glycol), mixtures thereof, and vegetable oil.

Parenteral dosage forms useful in accordance with the present invention can also be formulated as injectable prolonged release formulations in which the β-lactamase inhibitor is combined with one or more natural or synthetic biodegradable or biodispersible polymers such as carbohydrates, including starches, gums and esterified or esterified cellulosic derivatives, polyethers, polyesters, polyvinyl alcohols, gelatins, or alginates. Such dosage formulations can be prepared for example in the form of microsphere suspensions, gels, or shaped polymer matrix implants that are well-known in the art for their function as "depot-type" drug delivery systems that provide prolonged release of the biologically active components. Such compositions can be prepared using art-recognized formulation techniques and designed for any of a wide variety of drug release profiles.

CLAVULANIC ACID-TEST FOR NEUROPROTECTIVE ACTIVITY

N-Acetylaspartylglutamate (NAAG) is an abundant brain dipeptide present in synaptic vesicles and released upon neuronal stimulation. Immunohistochemical studies show NAAG is localized to glutamatergic pathways and suggest both NAAG and glutamate may be co-released tinder certain physiological conditions. NAAG functions, in part, to antagonize the effects of glutamate at the N-methyl-D-aspartate (NMDA) receptor by acting as a weak agonist, following release NAAG is hydrolyzed by membrane bound NAALADase liberating glutamate. Under pathological conditions of ischemia and seizure NAALADase generated glutamate exacerbates neuronal injury. It has been reported that blocking NAALADase reduces ischemic brain injury. Blocking NAALADase reduces the high levels of glutamate that follow ischemic stroke, protecting the brain from the neurotoxic effects of this excitatory neurotransmitter. To test the neuroprotective activity of clavulanic acid (CLAV) animals were treated with the neurotoxin kainate. Kainate stimulates glutamate receptors triggering generalized seizure and destruction of neurons particularly those localized to area CA3 of the hippocampus.

Experimental Procedure

Sixteen mail Sprague Dawley rats weighing between 300–350 gm were tested. One hour prior to kainate treatment eight animals were treated with clavulanic acid salt (CLAV) at an IP dose of 1 μg/kg while the remaining eight were given saline vehicle. Kainate was given IP at a dose of 25 mg(/kg. Over the next 60 minutes animals were observed for seizure activity. The first 10 minutes of this observation period was videotaped. Sixty minutes post kainate treatment animals were given another IP injection of CLAV or saline vehicle. Animals that survived kainate treatment were sacrificed seven days later and their brains examined for histological changes in the hippocampus. Three untreated control animals of the same weight and age as the experimental animals were sacrificed and their hippocampal morphology used as a standard for comparison.

Results

There was an ostensible difference in seizure activity between treatments. Animals given CLAV showed a longer onset to seizure and diminished seizure activity as compared to controls given saline vehicle. Indeed, four of the vehicle animals died within 24 hours of kainate treatment. There were no fatalities in the CLAV treated group. Histological inspection of the hippocampus revealed a dramatic difference in neuronal survival in area CA3. CLAV treated animals appear to have normal neuronal morphology and numbers in CA3 as compared to untreated controls.

Summary

The data demonstrate that CLAV is neuroprotective in the kainate seizure model. This finding supports the hypothesis that CLAV functions in part by blocking NAALADase. These compelling data predict that CLAV is useful to treat stroke, epilepsy, and other patient conditions presenting neuronal insult.

Neuroprotective Formulations

|      | β-lactamase inhibitor/dose (mg) | Carrier | Dosage Form |
|------|----------------------------------|---------|-------------|
| I.   | Clavulanic acid, potassium/30    | starch/maltose | capsule |
| II.  | Clavulanic acid, sodium/50       | microcrystalline cellulose/trehalose | tablet |
| III. | Tazobactam/75                    | saline | injectable |
| IV.  | Tazobactam/125                   | starch microspheres | injectable |
| V.   | Clavulanic acid, potassium/150   | saline | injectable |
| VI.  | Sulbactam/200                    | saline | injectable |
| VII. | Sulbactam/250                    | polylactide microspheres | injectable |

Patient Use (A) A patient is administered a dose of Formulation V above within 1.5 hours of suffering a stroke to reduce neuronal insult.

(B) A patient susceptible to recurrent seizures is administered Formulation I above three times a day.

(C) A patient with Parkinson's disease is administered Formulation V above twice a day to reduce neuronal degeneration.

(D) Formulation VI is administered to a stroke victim within 2 hours of the occurrence. Thereafter, Formulation VII is administered to the patient once a day for up to 3 weeks to minimize damage to neuronal tissues.

(E) Formulation V is administered to a newborn following an incident of possible perinatal asphyxia to prevent or reduce neuronal damage.

I claim:

1. A method of treatment of a patient suffering from or susceptible to a condition known to result in loss of neuronal cells or loss of neuronal cell function by reducing neuronal cell loss or function resulting from such condition said method comprising the step of administering to said patient a neuroprotective amount of a bacterial β-lactamase inhibitor.

2. A method for preventing neurons damage or the progression of neuronal damage in a patient suffering from or susceptible to disease states causing such neuronal damage, said method comprising the step of administering to the patient a neuroprotective amount of a bacterial β-lactamase inhibitor.

3. A method of treatment of a patient suffering from or susceptible to a condition known to result in or from loss of neuronal cells or loss of neuronal cell function by reducing loss of neuronal cells or neuronal cell function resulting from such condition, said method comprising the step of administering to said patient a neuroprotective amount of clavulanic acid, a pharmaceutically acceptable salt thereof, or an active ester thereof.

4. A method for preventing neuronal damage or the progression of neuronal damage in a patient suffering from or susceptible to such neuronal damage, said method comprising the step of administering to said patient a neuroprotective amount of clavulanic acid, a pharmaceutically acceptable salt thereof, or an active ester thereof.

* * * * *

UNITED STATES PATENT AND TRADEMARK OFFICE
CERTIFICATE OF CORRECTION

PATENT NO.    : 6,426,342 B2
DATED         : July 30, 2002
INVENTOR(S)   : Gary A. Koppel It is certified that error appears in the above-identified patent and that said Letters Patent is hereby corrected as shown below:

<u>Title page,</u>
Item [60], Related U.S. Application Data, change "Jan. 18, 2001" to
-- Jan. 18, 2000 --.

<u>Column 8,</u>
Line 13, change "neurons" to -- neuronal --.

Signed and Sealed this

Fourteenth Day of October, 2003

JAMES E. ROGAN
*Director of the United States Patent and Trademark Office*